US012109045B2

(12) United States Patent
Gonzales et al.

(10) Patent No.: US 12,109,045 B2
(45) Date of Patent: Oct. 8, 2024

(54) MOUTH GUARD HAVING USER-NOTIFICATION FEATURE OF IMPACT FORCE

(71) Applicant: Force Impact Technologies, Inc., Gilbert, AZ (US)

(72) Inventors: Anthony M. Gonzales, Canoga Park, CA (US); Robert M. Merriman, Gilbert, AZ (US); Susan M. Merriman, Gilbert, AZ (US); Christopher T. Cooper, Stittsville (CA)

(73) Assignee: Force Impact Technologies, Inc., Gilbert, AZ (US)

( * ) Notice: Subject to any disclaimer, the term of this patent is extended or adjusted under 35 U.S.C. 154(b) by 46 days.

(21) Appl. No.: 17/812,885

(22) Filed: Jul. 15, 2022

(65) Prior Publication Data

US 2022/0346711 A1   Nov. 3, 2022

Related U.S. Application Data

(63) Continuation of application No. 16/723,246, filed on Dec. 20, 2019, now Pat. No. 11,389,113.
(Continued)

(51) Int. Cl.
*A61B 5/00*     (2006.01)
*A61B 5/11*     (2006.01)
(Continued)

(52) U.S. Cl.
CPC ............ *A61B 5/682* (2013.01); *A61B 5/1126* (2013.01); *A61B 5/4064* (2013.01); *A61B 5/742* (2013.01);
(Continued)

(58) Field of Classification Search
None
See application file for complete search history.

(56) References Cited

U.S. PATENT DOCUMENTS

| 4,672,959 A | 6/1987 | May |
| 4,765,234 A | 8/1988 | Lake, Jr. |

(Continued)

FOREIGN PATENT DOCUMENTS

| CA | 2 816 982 | 5/2012 |
| CN | 201505230 | 6/2010 |

(Continued)

OTHER PUBLICATIONS

European Patent Office, Extended European Search Report for Application No. 22174642.3, dated Sep. 9, 2022 (12 pages).
(Continued)

*Primary Examiner* — Ronald Laneau
(74) *Attorney, Agent, or Firm* — Nixon Peabody LLP

(57) ABSTRACT

A mouth guard senses impact forces and determines if the forces exceed an impact threshold. If so, the mouth guard notifies the user of the risk for injury by haptic feedback, vibratory feedback, and/or audible feedback. The mouth guard system may also remotely communicate the status of risk and the potential injury. The mouth guard uses a local memory device to store impact thresholds based on personal biometric information obtained from the user and compares the sensed forces relative to those threshold values. The mouth guard and its electrical components on the printed circuit board are custom manufactured for the user such that the mouth guard provides a comfortable and reliable fit, while ensuring exceptional performance.

21 Claims, 8 Drawing Sheets

Related U.S. Application Data

(60) Provisional application No. 62/782,965, filed on Dec. 20, 2018.

(51) Int. Cl.

| | | |
|---|---|---|
| *A63B 71/08* | (2006.01) | |
| *B29C 51/12* | (2006.01) | |
| *B29C 51/26* | (2006.01) | |
| *B29C 51/30* | (2006.01) | |
| *B29K 23/00* | (2006.01) | |
| *B29L 31/00* | (2006.01) | |
| *B29L 31/52* | (2006.01) | |
| *G01C 17/02* | (2006.01) | |
| *G01C 19/00* | (2013.01) | |
| *G01P 15/00* | (2006.01) | |
| *G06F 3/01* | (2006.01) | |
| *G06F 3/16* | (2006.01) | |
| *H05K 1/02* | (2006.01) | |
| *H05K 1/18* | (2006.01) | |
| *H05K 3/28* | (2006.01) | |

(52) U.S. Cl.
CPC .......... *A61B 5/7455* (2013.01); *A63B 71/085* (2013.01); *B29C 51/12* (2013.01); *B29C 51/266* (2013.01); *B29C 51/30* (2013.01); *G01C 17/02* (2013.01); *G01C 19/00* (2013.01); *G01P 15/00* (2013.01); *G06F 3/016* (2013.01); *G06F 3/16* (2013.01); *H05K 1/028* (2013.01); *H05K 1/189* (2013.01); *H05K 3/284* (2013.01); *A61B 2503/10* (2013.01); *A61B 2560/0214* (2013.01); *A61B 2562/0219* (2013.01); *A63B 2220/40* (2013.01); *A63B 2220/53* (2013.01); *A63B 2225/50* (2013.01); *B29K 2023/083* (2013.01); *B29K 2909/14* (2013.01); *B29L 2031/52* (2013.01); *B29L 2031/768* (2013.01); *H05K 2201/09027* (2013.01); *H05K 2201/10037* (2013.01); *H05K 2201/10106* (2013.01); *H05K 2201/10151* (2013.01); *H05K 2201/10159* (2013.01); *H05K 2201/10545* (2013.01); *H05K 2203/1322* (2013.01); *H05K 2203/1327* (2013.01)

(56) References Cited

U.S. PATENT DOCUMENTS

| | | | |
|---|---|---|---|
| 4,977,905 A | 12/1990 | Kittleson | |
| 4,979,516 A | 12/1990 | Abraham, III | |
| 5,031,638 A | 7/1991 | Castaldi | |
| 5,203,351 A | 4/1993 | Adell | |
| 5,293,880 A | 3/1994 | Levitt | |
| 5,732,715 A | 3/1998 | Jacobs | |
| 6,092,524 A | 7/2000 | Barnes | |
| 6,178,967 B1 | 1/2001 | Barnes | |
| 6,299,441 B1 | 10/2001 | Novak | |
| 6,584,978 B1 | 7/2003 | Brett | |
| 6,941,952 B1 | 9/2005 | Rush, III | |
| 7,827,991 B2 | 11/2010 | Maher | |
| 7,950,394 B2 | 5/2011 | Elkin | |
| 8,133,054 B2 * | 3/2012 | Yamamoto | A61C 7/008 433/213 |
| 8,235,052 B2 | 8/2012 | Maurello | |
| 8,459,267 B2 | 6/2013 | Zimmerman | |
| 8,739,599 B2 | 6/2014 | Hennig | |
| 8,766,798 B2 | 7/2014 | Howard | |
| 8,945,919 B2 | 2/2015 | Mori | |
| 8,959,668 B1 | 2/2015 | Ganes | |
| 9,005,120 B2 | 4/2015 | Ryan | |
| 9,017,069 B2 | 4/2015 | Boyden | |
| 9,044,198 B2 | 6/2015 | Benzel | |
| 9,060,986 B2 | 6/2015 | Breitenbach | |
| 9,070,269 B2 | 6/2015 | Evans | |
| 9,149,227 B2 | 10/2015 | Benzel | |
| 9,226,707 B2 | 1/2016 | Huang | |
| 9,289,176 B2 | 3/2016 | Benzel | |
| 9,585,619 B2 | 3/2017 | Benzel | |
| 9,597,567 B1 | 3/2017 | Tran | |
| 9,849,364 B2 | 12/2017 | Tran | |
| 9,955,918 B2 * | 5/2018 | Paris | A61B 5/1126 |
| 9,968,777 B1 | 5/2018 | Demarest | |
| 9,975,033 B2 | 5/2018 | Tran | |
| 10,004,515 B2 | 6/2018 | Smith | |
| 10,010,694 B2 | 7/2018 | Lin | |
| 10,028,679 B2 | 7/2018 | Paris | |
| 10,092,814 B2 | 10/2018 | Wright | |
| 10,117,010 B2 | 10/2018 | Spector | |
| 10,172,555 B2 | 1/2019 | Cam | |
| 10,376,210 B2 * | 8/2019 | Paris | A61B 5/01 |
| 10,517,525 B2 | 12/2019 | Yoon | |
| 11,064,913 B2 | 7/2021 | Gonzales | |
| 11,109,808 B2 | 9/2021 | Yoon | |
| 11,179,104 B2 | 11/2021 | Gonzales | |
| 11,185,285 B2 * | 11/2021 | Lathrop | A61B 5/02438 |
| 11,389,113 B2 | 7/2022 | Gonzales | |
| 11,432,767 B2 | 9/2022 | Gonzales | |
| 11,510,618 B2 | 11/2022 | Gonzales | |
| 11,607,171 B2 | 3/2023 | Gonzales | |
| 2003/0154990 A1 | 8/2003 | Parker | |
| 2004/0112389 A1 | 6/2004 | Abraham | |
| 2005/0113654 A1 | 5/2005 | Weber | |
| 2006/0065277 A1 | 3/2006 | Weber | |
| 2006/0073433 A1 | 4/2006 | Anderson | |
| 2007/0061106 A1 | 3/2007 | Vock | |
| 2007/0151567 A1 | 7/2007 | Maurello | |
| 2008/0060661 A1 | 3/2008 | Mathias | |
| 2008/0269579 A1 | 10/2008 | Schiebler | |
| 2009/0210032 A1 | 8/2009 | Beiski | |
| 2011/0179851 A1 * | 7/2011 | Mack | A42B 3/046 264/16 |
| 2011/0181419 A1 | 7/2011 | Mack | |
| 2011/0184319 A1 | 7/2011 | Mack | |
| 2011/0184663 A1 | 7/2011 | Mack | |
| 2011/0214478 A1 | 9/2011 | Hennig | |
| 2011/0218455 A1 | 9/2011 | Hennig | |
| 2012/0143526 A1 | 6/2012 | Benzel | |
| 2012/0172677 A1 | 7/2012 | Logan | |
| 2013/0074248 A1 | 3/2013 | Evans | |
| 2013/0110415 A1 | 5/2013 | Davis | |
| 2013/0211270 A1 | 8/2013 | St. Laurent | |
| 2014/0024971 A1 | 1/2014 | Bunn | |
| 2014/0261464 A1 | 9/2014 | Layzell | |
| 2014/0290669 A1 * | 10/2014 | Ngo | A63B 71/085 128/861 |
| 2014/0312834 A1 | 10/2014 | Tanabe | |
| 2014/0335464 A1 | 11/2014 | Boyden | |
| 2015/0119759 A1 | 4/2015 | Gonzales | |
| 2015/0173666 A1 | 6/2015 | Smith | |
| 2015/0173856 A1 | 6/2015 | Lowe | |
| 2015/0238142 A1 | 8/2015 | Djordjevski | |
| 2015/0305671 A1 | 10/2015 | Yoon | |
| 2016/0022167 A1 | 1/2016 | Simon | |
| 2016/0106346 A1 | 4/2016 | Benzel | |
| 2016/0107067 A1 | 4/2016 | Barnes | |
| 2016/0158627 A1 | 6/2016 | Layzell | |
| 2016/0158628 A1 | 6/2016 | Layzell | |
| 2016/0158629 A1 | 6/2016 | Lin | |
| 2016/0236051 A1 | 8/2016 | Esteves | |
| 2016/0242692 A1 | 8/2016 | McAuliffe | |
| 2017/0020434 A1 | 1/2017 | Walker | |
| 2017/0042272 A1 | 2/2017 | Ferguson | |
| 2017/0071538 A1 | 3/2017 | Calcano | |
| 2017/0095204 A1 | 4/2017 | Stitzel | |
| 2017/0146555 A1 | 5/2017 | Wang | |
| 2017/0224252 A1 | 8/2017 | Salzar | |
| 2017/0238850 A1 | 8/2017 | Gonzales | |
| 2017/0266536 A1 | 9/2017 | Sciortino | |
| 2017/0282451 A1 | 10/2017 | Layzell | |
| 2017/0296897 A1 | 10/2017 | Simpson | |
| 2017/0345536 A1 | 11/2017 | Letizia | |
| 2017/0357241 A1 | 12/2017 | Huang | |

(56) References Cited

U.S. PATENT DOCUMENTS

| | | | |
|---|---|---|---|
| 2018/0021659 A1 | 1/2018 | Layzell | |
| 2018/0005167 A1 | 3/2018 | Wisniewski | |
| 2018/0056167 A1 | 3/2018 | Wisniewski | |
| 2018/0070668 A1 | 3/2018 | Stephens | |
| 2018/0078843 A1 | 3/2018 | Tran | |
| 2018/0154242 A1 | 6/2018 | Austin | |
| 2018/0196079 A1 | 7/2018 | Austin | |
| 2018/0242911 A1* | 8/2018 | Paris | A61B 5/6803 |
| 2018/0264347 A1 | 9/2018 | Tran | |
| 2018/0275119 A1 | 9/2018 | Podoly | |
| 2018/0326291 A1 | 11/2018 | Tran | |
| 2019/0105842 A1 | 4/2019 | Dau | |
| 2019/0125261 A1* | 5/2019 | Lathrop | H01M 16/003 |
| 2020/0147473 A1 | 5/2020 | Maloney | |
| 2020/0196947 A1* | 6/2020 | Gonzales | A61B 5/1126 |
| 2020/0345536 A1 | 11/2020 | Letizia | |
| 2020/0367821 A1 | 11/2020 | Redshaw | |
| 2022/0104768 A1 | 4/2022 | Vegar | |
| 2022/0280108 A1* | 9/2022 | Gonzales | A61B 5/7282 |

FOREIGN PATENT DOCUMENTS

| | | |
|---|---|---|
| CN | 203468806 | 3/2014 |
| CN | 102599674 | 7/2014 |
| CN | 106110390 | 11/2016 |
| CN | 105030767 | 2/2018 |
| CN | 108124797 | 6/2018 |
| CN | 108613575 | 10/2018 |
| CN | 109011414 | 12/2018 |
| EP | 1 901 749 | 3/2008 |
| EP | 3 064 242 | 9/2016 |
| GB | 2570726 A | 8/2019 |
| GB | 2577939 A | 4/2020 |
| JP | 2000-070292 A | 3/2000 |
| JP | 2012-147280 A | 8/2012 |
| WO | WO 2016/168939 | 10/2016 |
| WO | WO 2017/070343 | 4/2017 |
| WO | WO 2017/091708 | 6/2017 |

OTHER PUBLICATIONS

So Adrienne; "This Smart Mouthguard Can Monitor Concussions"; WIRED; Mar. 1, 2018; retrieved from https://www.wired.com/stoy/this-smart-mouthguard-can-monitor-concussions/ on Aug. 30, 2022 (3 pages).

U.S. Appl. No. 17/816,942, filed Aug. 2, 2022, Gonzales, Anthony M., Mouth Guard having Low-Profile Printed Circuit Board for Sensing and Notification of Impact Forces.

So, A. et al.; "This Smart Mouthguard Can Monitor Concussions"; WIRED, Mar. 1, 2018; retrieved from https://www.wired.com/stoy/this-smart-mouthguard-can-monitor-concussions/ on Aug. 30, 2022 (3 pages).

Greenwald, R. M. et al., "Head Impact Severity Measures for Evaluating Mild Traumatic Brain Injury Risk Exposure," Neurosurgery 62(4):789-798, Apr. 2008.

Rowson, S. et al., "Linear and Angular Head Acceleration Measurements in Collegiate Football," Journal of Biomechanical Engineering, vol. 131, pp. 061016-1 to 061016-7, ASMA. Jun. 20098.

Simma. B. et al., "Mild head injury in pediatrics: algorithms for management in the ED and in young athletes," American Journal of Emergency Medicine 31, pp. 1133-1138, 2013.

Graham, R. et al., "Sports-related concussions in Youth: Improving the Science, Changing the Culture," National Academies of Sciences, 2013.

Walilko, T. J., "Biomechanical Response of the Temporomandibular Join from Impacts in Boxing," Wayne State University, 2004.

Broglio, S. P., "The Biomechanical Properties of Concussions in High School Football," Med Sci Sports Exerc., 42(11):2064-2071, Nov. 2010.

Gurdjian, E. S., J. Trauma, 6(5):600-4, Sep. 1966.

Camarillo, D., "Head contacts in collegiate football measured with an instrumented mouthguard," Br. J. Sports Med., Abstracts from the 4$^{th}$ International Conference on Concussion in Sport, Zurich. 2012, doi: 10.1136/bjsports-2012-092101.33.

Rowson, S. & Duma, S. M., "Development of the star evaluation system for football helmets: Integrating player head impact and risk of concussion," Ann. Biomed. Eng. 39, pp. 2130-2140, 2011.

Rowson, S. & Duma, S. M., "Brain Injury Prediction: Assessing the Combined Probability of Concussion Using Linear and Rotational Head Acceleration," Annals of Biomedical Engineering, 41(5):873-882, May 2013.

Rowson, S. et al., "Rotational Head Kinetics in Football Impacts: An Injury Risk Function for Concussion," Annals of Biomedical Engineering, 40(1): 1-13, Jan. 2013.

Camarillo, D. et al., "An Instrumented Mouthguard for Measuring Linear and Angular Head Impact Kinematics in American Football," Annals of Biomedical Engineering, 41(9):1939-1949, Sep. 2013.

Benjamin Watkins Industrial Design, "X2 Impact Mouthguard," Retrieved from internet, <https://www.behance.net/gallery/X2-Impact-DVT2-Mouthguard/2891933/> Oct. 25, 2013.

Viano. "Football Helmet Drop Tests on Different Fields Using an Instrumented Hybrid III Head," Annals of Biomedical Engineering, 40(1):97-105, Jan. 2012.

International Search Report and Written Opinion in International Application No. PCT/US2019/068021, mailed Jun. 24, 2020 (16 pages).

\* cited by examiner

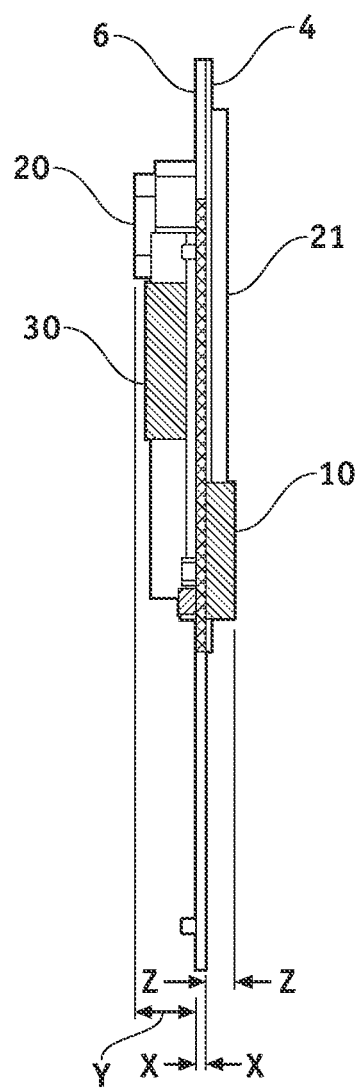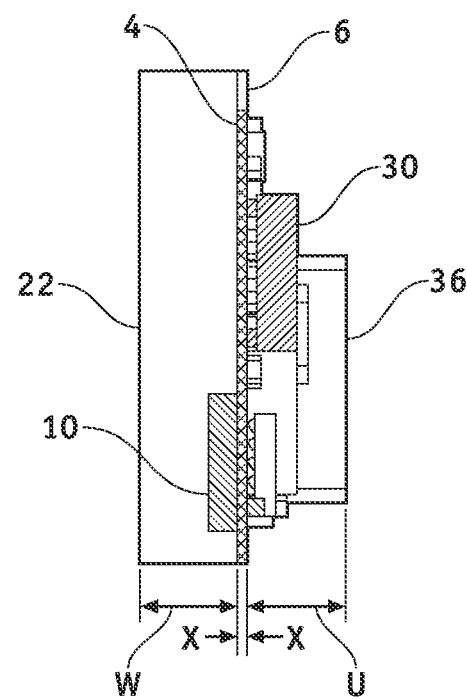
FIG. 4A
FIG. 4B

MOUTH GUARD HAVING USER-NOTIFICATION FEATURE OF IMPACT FORCE

CROSS REFERENCE TO RELATED APPLICATIONS

The present application is a continuation of U.S. application Ser. No. 16/723,246, filed on Dec. 20, 2019, now allowed, which claims priority to Provisional Patent Application No. 62/782,965, filed Dec. 20, 2018, and each of which is incorporated herein by reference in its entirety.

COPYRIGHT

A portion of the disclosure of this patent document may contain material which is subject to copyright protection. The copyright owner has no objection to the facsimile reproduction by anyone of the patent disclosure, as it appears in the Patent and Trademark Office patent files or records, but otherwise reserves all copyright rights whatsoever

FIELD OF THE INVENTION

The present invention relates generally to wearable devices for the detection of injurious concussive forces. More particularly, this invention relates to a mouth guard with on-board electronics for sensing external impact forces, transforming such data, communicating risk levels locally to the user and remotely to other devices.

BACKGROUND OF THE INVENTION

At all levels, athletics are seen as constructive methods of exercise. Sports encourage robust competition and health. Men, women, boys, and girls participate in a variety of sports and athletic activities on a formal and informal basis. Given the variety of individuals involved, there is a large number of activities and sports played by many diverse player types. Some games involve high-speed running. And some involve more physical sports with purposeful or incidental contact between players and/or fixed objects. Contact raises the potential for harm, including head and brain injury. While American football is seen as a primary cause of sports concussions and long-term brain injury, it is less known that players in other sports also experience a high-risk for head injury and brain trauma. For instance, the incidence of concussions in girls' soccer is second only to football, and the combined incidence of concussions for boys' and girls' soccer nearly matches that of football.

Virtually any forceful impact to the head or body involves some risk level for brain trauma. Head injury may occur from collision with another player, an object, or even from a fall. Impact and rotational forces to the head are the leading causes for injury. Brain injury manifests as either neural, or most often, vascular injury within the head.

It is also widely known that the risk and severity of brain injury is related to the frequency and severity of repeated head trauma. A first blow to the head may modify the risk factors for future injury. For instance, a first incidental hit may lower the threshold for injury due to a later fall to the ground. Repeated blows and impacts have a greater impact on the risk of head trauma. Even a minor blow, below the normal threshold for injury, may cause catastrophic brain injury if it follows an earlier risk-elevating first impact. Furthermore, biometric information (i.e., sex, age, height, weight, etc.) provides an additional factor that is needed to determine the impact threshold for predicting brain injury for a particular individual.

During sports play, head injury may manifest as a temporary impairment or loss of brain function. However, more severe concussions may cause a variety of physical, cognitive, and emotional symptoms. Unfortunately, some injuries cause no immediate or obvious observable symptoms, and even minor symptoms may be overlooked, especially during the excited flow of a game. The unknown consequences of prior impacts further exacerbate the risks, by failing to diagnose an injury and take corrective action.

In recent studies, the CDC estimates that about 40% to 50% of athletes will not self-report that they may have suffered a concussive blow. While some portion of these athletes who fail to report head injuries are likely out of stubbornness, the failure to report is often attributed to the player not experiencing traditional or expected concussion symptoms. Consequently, notifying the user that he or she has received a significant impact (or impacts) is necessary for the user to report the event.

Considering the high-risk of injury in various sports and activities (such as personal fitness programs), prior art solutions have not provided a solution that is flexible and precise enough for use in the myriad of routines for the entire spectrum of athletes. For instance, given the extent of electronics and monitoring systems required for head injury assessment tools, products to be worn by players often involve a skull cap or complete helmet. A helmet, while welcomed in permissive contact sports such as football, hockey and motocross, might be out-of-place for tennis, interfere with play for a sport such as soccer, and even presents an added danger on the rugby pitch. Furthermore, prior art solutions have traded accuracy for comfort, or otherwise required a comprise sacrificing either the usefulness of information or wearing compliance with the user.

Other products include multiple part pieces that are deployed at different parts of the player's body and can be cumbersome and/or complicated to employ. Additionally, other solutions do not provide a simple, customizable, single-piece portable solution.

Clinical tests have proven that the combined measurement of linear and angular acceleration has the most accurate prediction of concussion possibilities, compared to either of the measurements independent of one another. Clinical studies suggest that sensors located in a mouth guard, as opposed to an accessory on a helmet or a chinstrap, have a higher correlation to the center of gravity of the brain. This is thought to be a result of the mouth guard's placement in relation to the rear molars, which are attached to the base of the skull. Certain anatomical landmarks on the head, such as in the inner ear, are considered by some to be effective in correlating impacts to brain injury. However, due to the size and quantity of the components required to ensure proper detection, as well as the relative locations of components, the spatial arrangement and structure of such devices have been unable to achieve a useful device that is ergonomically acceptable and a comfortable fit for the user.

The present invention resolves many of these issues by providing a mouth guard that reliably identifies impact forces that may cause a head injury and notifies the user of that impact event. The inventive mouth guard is not only customizable to the user and is comfortable to wear, but is constructed through a simplistic manufacturing process.

All these and other objects of the present invention will be understood through the detailed description of the invention below.

SUMMARY OF THE INVENTION

The present invention is directed to an impact sensing device and system for communicating information about impacts and user status. A mouth guard vibrates, creates a tone, sends a local signal, and/or otherwise indicates the impact to the user. In one embodiment, a piezoelectric vibration may create a tone that is only audible to the wearer via bone conduction.

In one aspect, the present invention is a mouth guard for measuring impact forces and determining possible concussive risk and brain injury. The mouth guard device is able to detect and measure the impact force to an athlete's head during activities by use of an array of motion and accelerometer sensors. The mouth guard preferably contains a sensor array, a battery, a (wireless) power receiver with charging circuit, communications system (such as a Bluetooth low-energy transceiver), a mechanical indicator (e.g., piezo transducer), and a light indicator (e.g., an RGB LED indicator). The sensors are designed to measure force, and correlate such forces with predetermined impact thresholds, preferably for linear and angular forces. Preferably, those predetermined impact thresholds may be later modified automatically while the user is participating in the activity in response to one or more impacts to the head. The system is also capable of determining impacts caused when the device is worn in place, as opposed to impacts when the device is being handled in other manners (e.g., when the user drops the mouth guard). The electrical components are provided on a flexible printed circuit board (PCB) that is configured to have a low profile that provides user comfort, despite being embedded within the mouth guard. The mouth guard may be charged by a wireless power transmitter that sources power from a standard USB power adapter.

Regarding notification of an impact, the mouth guard may provide the user with local and/or remote notification. Local notification may include a notification component (e.g., piezoelectric, haptic, and/or magnetic device) that operates to create an audible tone (e.g., 2-4 kHz) that is conducted generally along the bone and skull. Local notification may include an audible tone, bone conduction signal, vibration, and/or other haptic feedback. Additionally, a local notification may include a light indication (e.g., LED) on the mouth guard of a certain color and/or pattern representing the level of risk and/or injury, which may be noticed by other individuals (e.g., referees, coaches, other players, etc.) who see the light indicator in the mouth guard of the user. Of course, the user who removes the mouth guard will notice the light indicator as well. The light may be turned off, leaving a local and a remote notification in place. Remote location may be sent via telecommunication to a remote receiver, such as a smart phone, with a software application prepared to receive incoming information and display to a remote user. Multiple wearable devices may each be assigned to separate users, and the remote receiver may manage signals from multiple devices, such as a coach of a team simultaneously monitoring each individual player during a practice session or game.

In another aspect, the inventive mouth guard system for detection impact forces comprises a main body, at least one sensor, and a notification component. The main body comprises flexible material and has a front portion with a generally arched-shaped peripheral side for facing the buccal region of a mouth of a user. The main body further includes a depressed portion adjacent to the front portion that is sized and shaped to receive teeth of the user. The at least one sensor detects a force and is embedded in the flexible material. The at least one sensor is located within the front portion. The notification component is embedded within the flexible material and generates mechanical energy. The notification component activates in response to the at least one sensor detecting a force above a predetermined force threshold.

In another aspect, the inventive mouth guard system comprises main body, a printed circuit board, a processor, a linear force sensor, a rotational force sensor, and a notification component. The main body is comprised of flexible material and has a front portion with a generally arched-shaped peripheral side for facing the buccal region of a mouth of a user. The main body further includes a depressed portion adjacent to the front portion that is sized and shaped to receive teeth of the user. The printed circuit board is embedded within the flexible material in the front portion and extends along a substantial portion of the arched-shaped peripheral side. The processor is located on the printed circuit board. The linear force sensor and the rotational force sensor are located on the printed circuit and are in communication with the processor. The notification component generates mechanical energy and is located on the printed circuit board. And, wherein, in response to at least one of the linear sensor and the rotational sensor detecting a force above a predetermined force threshold, the processor activates the notification component to produce a feedback to be sensed by the user.

In yet a further aspect, the present invention is a method for indicating a high impact force to a user wearing a mouth guard. The method comprises detecting at least a first impact event with at least one of a linear force sensor and a rotational force sensor embedded in the mouth guard, and determining whether a force associated with the first impact event exceeds a predetermined threshold. The method further includes, in response to the force exceeding a predetermined threshold, generating mechanical energy with a notification component to inform the user that the predetermined threshold has been exceeded. The notification component is embedded within the mouth guard and provide at least one of a haptic feedback, a vibratory feedback, or an auditory feedback to the user.

In yet another aspect, the present invention relates to a mouth guard system for detection impact forces. The mouth guard system includes a main body and a printed circuit board. The main body is comprised of flexible material and has a front portion with a generally arched-shaped peripheral side for facing the buccal region of a mouth of a user. The main body further includes a depressed portion adjacent to the front portion that is sized and shaped to receive teeth of the user. The front portion includes a centerline to be located generally adjacent to the incisors and two ends to be located generally adjacent to the right and left molars. The printed circuit board is embedded within the flexible material in the front portion of the main body and has a length extending along a substantial portion of the arched-shaped peripheral side. The printed circuit board includes a front side facing toward the buccal region of the mouth and a back side facing toward the teeth of the user. The printed circuit board includes components for detecting and indicating an impact force above a predetermined threshold. The components include at least a processor, a memory device, a force sensor, a battery, and a light indicator. The light indicator is located on the front side of the printed circuit board at the center of the front portion and is activated in response to an impact force exceeding a predetermined threshold. The force sensor is located on the back side of the printed circuit board near the center of the front portion of the main body. The processor and memory device are located on the back side of the printed circuit board. The battery is located on the front side of the printed circuit board adjacent to one of the ends.

In another aspect, a mouth guard system for detection of impact forces comprises a main body and a printed circuit board. The main body comprises a flexible material and has a front portion with a generally arched-shaped peripheral side for facing the buccal region of a mouth of a user. The main body further includes a depressed portion adjacent to the front portion that is sized and shaped to receive teeth of the user. The front portion includes a center to be located generally adjacent to the incisors and two ends to be located generally adjacent to the right and left molars. The printed circuit board is embedded within the flexible material in the front portion of the main body and has a length extending along a portion of the arched-shaped peripheral side. The printed circuit board includes a front side facing toward the buccal region of the mouth and a back side facing toward the teeth of the user. The printed circuit board includes components for detecting and indicating an impact force above a predetermined threshold. The components include at least a processor, a memory device, a first force sensor, a second force sensor, a battery, and an indicator for activation in response to an impact force exceeding the predetermined threshold. The printed circuit includes a middle portion with a length that is at least about 25% of the overall length of the printed circuit board. The middle portion has a width in the range of 6 mm to 15 mm and includes two cut-outs to enhance the bendability of the printed circuit board. The processor, the memory device, the first force sensor, and the second force sensor are mounted in the middle portion.

In yet another aspect, the invention relates to a method for manufacturing a custom mouth guard that detects impact forces of a user. The method comprises conforming a first layer of material to a model of the user's maxillary region that includes replicated teeth and, while the first layer of material is on the model and after the conforming, heating the first layer of material. The method further includes forcing a flexible printed circuit board into the heated first layer to force a plurality of components extending away from the flexible printed circuit board to be impressed into the first layer. The flexible printed circuit board includes linear and rotational force sensors. The method also includes overlaying a second layer of material over the flexible printed circuit board and the first layer, and conforming the second layer of material to exposed surfaces of the flexible printed circuit board and the first layer to create the custom mouth guard.

In another aspect, the invention is a method for manufacturing a custom mouth guard that detects impact forces of a user. The method comprises receiving biometric information associated with the user and storing impact threshold data on a memory of a flexible printed circuit board. The impact threshold data is based on the biometric information. The method further includes, after the receiving and the storing, conforming a first layer of material to a model of the user's maxillary region that includes replicated teeth. The method also includes forcing the flexible printed circuit board into the first layer to impress electrical components on the flexible printed circuit board into the first layer, and conforming the second layer of material to exposed surfaces of the flexible printed circuit board and the first layer to create the custom mouth guard.

In yet another aspect, the invention includes a method for manufacturing a custom mouth guard that detects impact forces of a user. The method comprises receiving a stone model of the user's maxillary region that includes replicated teeth, and receiving biometric information for the user. The biometric information at least includes the age and sex of the user. The method includes determining impact threshold data for the user based on the biometric information, and uploading the impact threshold data onto a memory device that is mounted on a flexible printed circuit board. The flexible printed circuit board has other components mounted thereon including a linear force sensor, a rotational force sensor, a processor, and a battery. The method further includes conforming a first layer of material to the stone model of the user's maxillary region, and while the first layer of material is on the model, heating the first layer of material. The method also includes forcing the flexible printed circuit board into the heated first layer to force a plurality of the components from the flexible printed circuit board to be impressed into the heated first layer, and conforming a second layer of material to exposed surfaces of the flexible printed circuit board and the first layer. The conforming includes impressing some of the components on the printed circuit board into the second layer of material.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

The present invention will be described with greater specificity and clarity with reference to the following drawings, in which:

FIG. 4A illustrates a left side profile view of the flexible printed circuit board assembly along the 4A-4A line in FIG. 1;

FIG. 4B illustrates a right side profile view of the flexible printed circuit board assembly along the 4B-4B line in FIG. 1;

Figure 1:
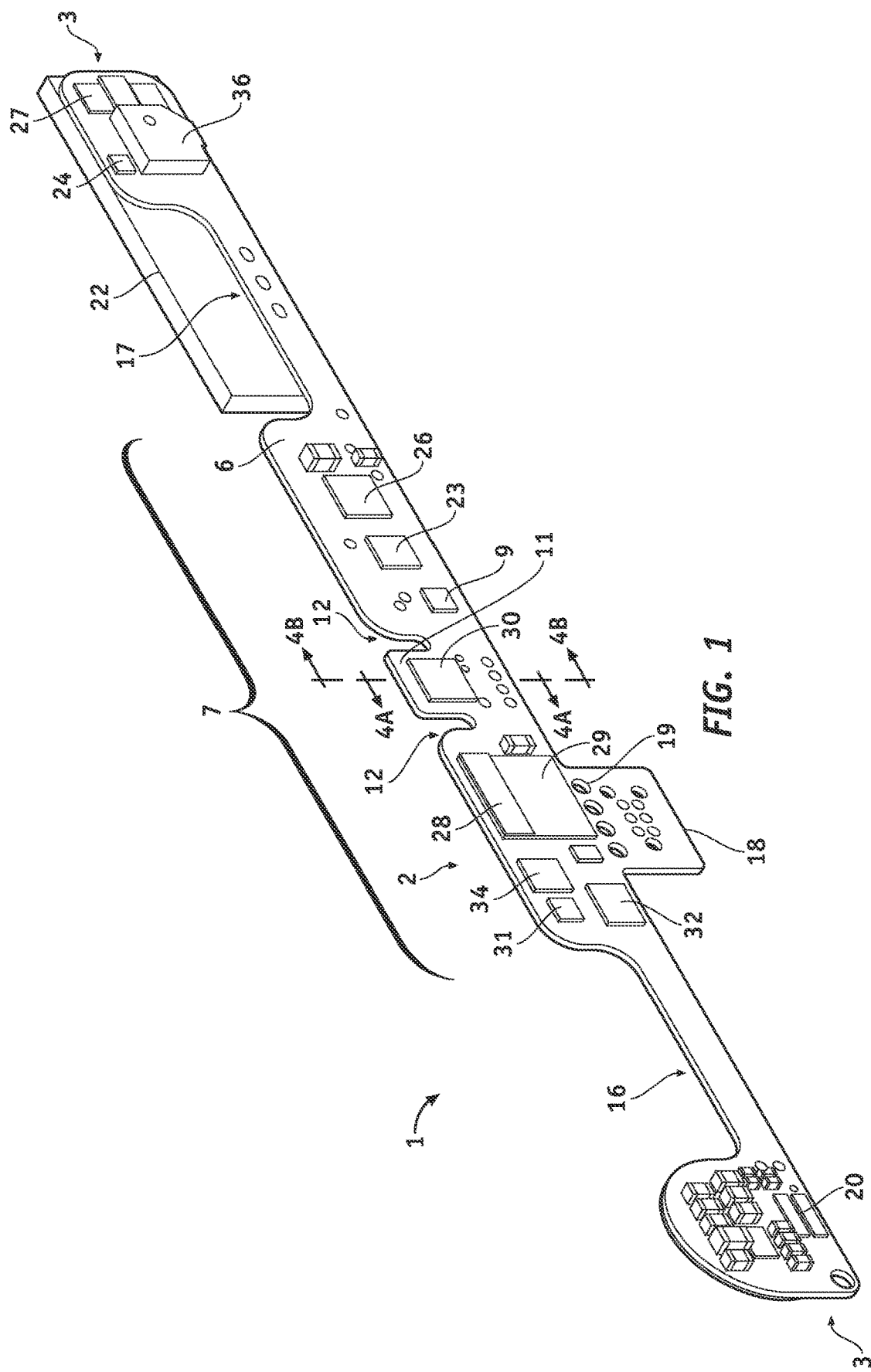
FIG. 1 illustrates a perspective view of the back side of a flexible printed circuit board assembly of an embodiment of the present invention.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE DRAWINGS

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

Figure 7:
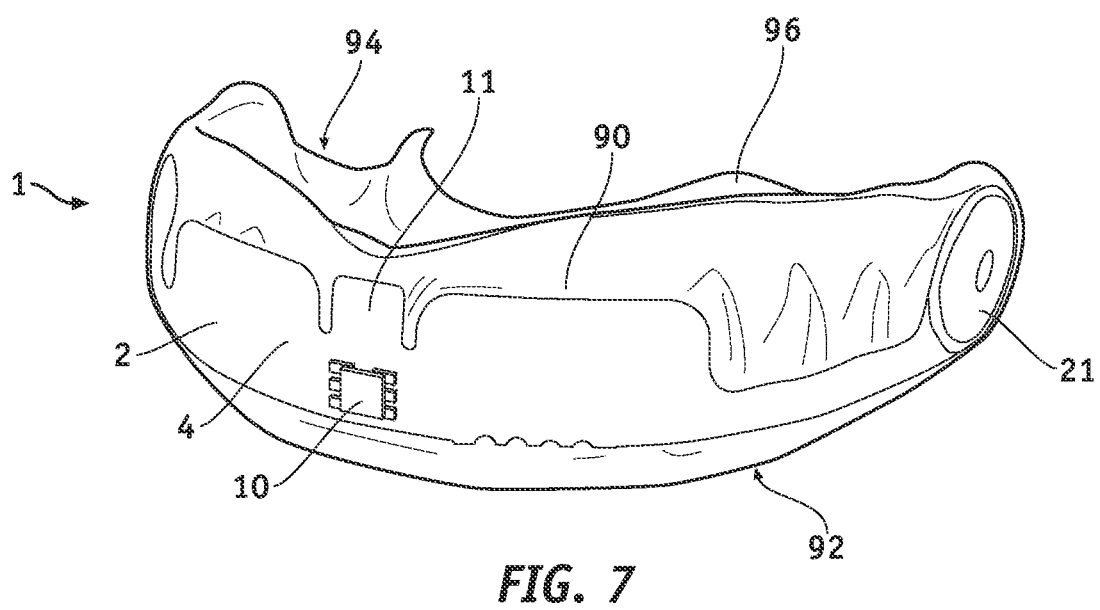
FIG. 7 illustrates the finished mouth guard from the manufacturing process of FIGS. 6A to 6D.

A mouth guard 1, shown best in FIG. 7, includes a flexible printed circuit board (PCB) and electronic components mounted thereon, which define a printed circuit board assembly (PCBA) 2. The PCBA 2 is designed and shaped for placement within the mouth guard 1, which is custom-fit for an athlete's mouth. The electronic components are encased within the flexible material of the mouth guard 1. The PCBA 2 is also flexible and designed with minimal structural dimensions (length, height, width, depth, etc.) for flexing and pivoting to conform to the contours of the mouth guard 1 during manufacturing and use. In one aspect, the invention herein focuses on the novel arrangement of the electronic components on the PCB A 2 to achieve efficient manufacturing, excellent operational performance, and user comfort.

The mouth guard 1 can detect and measure impacts to an athlete's head during sports activities. An array of motion and accelerometer sensors (discussed below) detect and measure an acceleration on the user, which can then be calculated into force data. The impact data is stored on the mouth guard and may be later or contemporaneously transmitted via a transmitter (e.g., a Bluetooth low energy transceiver) to a remote smart device, such as a phone or tablet, or like device (see FIG. 8). Additional information regarding the mouth guard is disclosed in co-owned U.S. Publication No. 2017/0238850 ("Impact Sensing Wearable Device and Method"), which is hereby incorporated by reference in its entirety.

As can be seen in FIG. 1, the PCBA 2 has a length that is defined between two end portions 3 that are intended to rest along the buccal side of the molars. The PCBA 2 includes a front side 4, which will face the buccal region of the wearer after incorporation in the mouth guard 1, and a back side 6 that will face the teeth. A middle portion 7 of the PCBA 2 is positioned between the two end portions 3 and generally has a length between about 25% and 50% of the overall length of the PCBA 2. The electrical components are primarily mounted within the middle portion 7. In one preferred embodiment, the middle portion 7 is about 40% of the overall length of the PCBA 2.

A center tab 11 is located within the middle portion 7 and is positioned in the front center of the mouth near the midline of the user's incisors. The center tab 11 is defined by a pair of cutouts 12 that provide the middle portion 7 with the ability to twist and bend as required during fabrication of the mouth guard 1, as discussed below with respect to FIG. 6. As such, the cutouts 12, which allow for dual axis rotation and twisting at pivot points adjacent thereto, allow the PCBA 2 to overcome the challenges of conforming within the custom mouth guard 1. The two cutouts 12 have a length that is at least 30% of the overall width of the middle portion 7. The middle portion 7 requires the additional bendability because it will be located along the region having the smallest radius of curvature in the dental arch (and, thus, in the mouth guard 1). The bridge portions 16, 17 of the PCBA 2 connect the end portions 3 and the middle portion 7 and are created by larger cut-outs to create a smaller dimension within the bridge portions 16, 17 for enhanced bendability of the PCBA 2.

The components are preferably soldered onto PCBA 2 and an underfill (preferably a non-viscous epoxy) is used to fill in spaces within the PCBA 2 to provide some level of rigidity to the PCBA 2. The electrical components on the PCBA 2 are preferably attached with minimal solder. The largest dimension of each of the electronic components is vertically oriented when possible to accommodate bending of the PCBA 2, meaning the long edge is arranged from top-to-bottom while the short edge runs laterally along the length of the PCBA 2. Some components cannot be vertically oriented, such as a wireless charging receiver 20 and a battery 22, and, thus, are preferably placed near the end portions 3 of the PCBA 2, which will be placed along an anatomic region having a larger radius of curvature (i.e., straighter) than the middle portion 7. The PCBA 2 is preferably made of a multilayered board design to act as primary carrier of all electronic components in the mouth guard 1, as discussed below with reference to FIG. 3.

Figure 2:
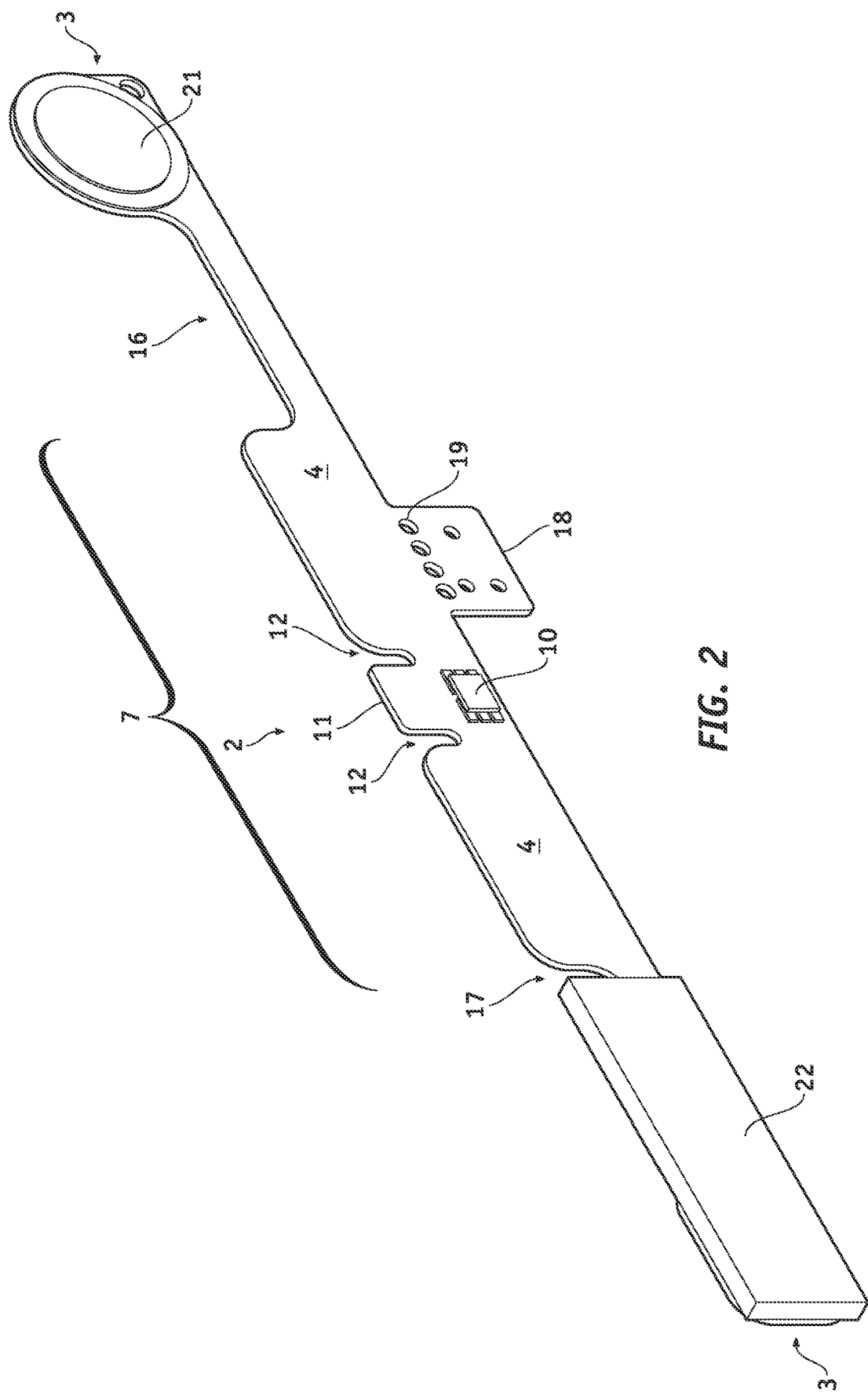
FIG. 2 illustrates a perspective view of the front side of the flexible printed circuit board assembly of FIG. 1.

The wireless charging receiver 20 is set on the front side 4 of the PCBA 2. As shown in FIG. 2, the wireless charging coil 21 is set opposite to a charging receiver 20. The charging receiver 20 includes power circuit with inductors and capacitors, and further includes an integrated circuit controller located in proximity to and in electrical communication (e.g., wired) with the wireless charging receiver 20. The wireless charging receiver 20 and the wireless charging coil 2 are preferably set along on of the molar ends 3 and configured to best receive the energy from the external charging station (not shown). As such, the charging coil 21 may be manipulated during the manufacturing process (FIG. 6) to ensure proper positioning so as to minimize skewing relative to the peripheral side surface of the mouth guard 1 that faces the buccal surface.

Regarding the force-sensing components, the PCBA 2 includes a high-G (high-gravity) accelerometer 30, a magnetometer 31 (which includes a digital compass), and a combination low-G (low gravity) accelerometer/gyroscope 32. The magnetometer 31 and the combination low-G (low gravity) accelerometer/gyroscope 32 form an inertial measurement unit (IMU) in that they provide data that is used for sensing the orientation of the mouth guard 1. The data provided by the IMU is utilized in a sensor-fusion algorithm, which is computed in the processor to implement a sensing feature that detects the orientation of the PCBA 2 and the mouth guard 1 in three-dimensional space. The combination low-G (low gravity) accelerometer/gyroscope 32 (hereinafter "gyroscope 32") can also be provided as two separate components, such that they are not packaged together. Alternatively, the magnetometer 31 can be packaged with the low-G (low gravity) accelerometer/gyroscope 32. The gyroscope 32 also provides data regarding angular velocity, which can be used to determine the angular acceleration (and rotational force) associated with the impact. Though these sensors 30, 31, 32 are measuring velocity and acceleration, they are herein considered to be linear and rotational force sensors because their sensed data correlates to the corresponding force and permits the processor to calculate it, as necessary.

The approximate location of the impact is computed using the IMU orientation result at the time of the impact and a calculated 3D linear acceleration impact vector. The 3D linear acceleration impact vector (relative to the mouth guard 1) is calculated using the data collected by the high-G accelerometer 30 at the moment of impact. In summary, the data received by the high-G accelerometer 30, the magnetometer 31, and the low-G accelerometer/gyroscope 32 can be used to provide information regarding the amount of linear force associated the impact, the amount of rotational force associated the impact, the spatial orientation of the impact, and movement data of the user.

Data from the high-G accelerometer 30, the magnetometer 31, and the gyroscope 32 is received and processed in a processor 28, which utilizes a memory 34 (preferably a flash memory) to correlate, relate, and otherwise store information for processing and communicating impact data. The memory 34, which may store impact data permanently or be erasable, may be located anywhere on the PCBA 2, but is preferably near the processor 28 to minimize latency. The processor 28 is further coupled with low energy Bluetooth transceiver 29. The Bluetooth transceiver 29 may include a radio and an embedded processor. The processor 28 collects data, stores the data in memory 34, and transmits the data via Bluetooth transmission, as necessary. It should be understood that while a single memory 34 is illustrated on the PCBA 2, it may have multiple memory devices 34. For example, the processor 28 may include its own memory device.

A serial wire debug (SWD) port 18 on the PCBA 2 allows wired access for initial programming of the processor(s) 28. In one embodiment, the initial programming data, such as impact thresholds based on the biometric data of the user, are stored in a memory device associated with the processor 28, while the impact data received by the sensing components is stored in the memory 34 showing in FIGS. 1-2. The user typically provides his or her biometric data when ordering the custom mouth guard 1. The biometric data of the user may include, but is not limited to: age, sex, weight, height, skull circumference, head shape (e.g., from photos of the sides, back, and/or front of the head), head mass (e.g., from a scan of the head), and/or prior concussion data. The biometric data may further include dimensional data taken from the maxilla of the user, such as from a stone model as discussed below with respect to FIG. 6. For example, the combination of the skull circumference along the forehead and the dimensional data of the maxilla provide s data that correlates to the mass of the head. Alternatively, a standard mass of the head may be estimated based on the age, sex, weight, and/or height of the user using commonly known biometric information. Assuming that standard mass is known, it can then be adjusted based on measurements of the specific measurements of the user's skull and/or maxilla data. In other words, a user having a skull circumference that is 10% larger than the standard skull circumference for someone of his same age, weight, and height may have the standard mass increased by 5% due to the larger-than-standard skull circumference. Examples of linear and rotational force risk factors and threshold data for different individuals are disclosed in co-owned U.S. Publication No. 2017/0238850 ("Impact Sensing Wearable Device and Method"), which is hereby incorporated by reference in its entirety.

The biometric data of the user is used to set initial thresholds for impact forces (e.g., rotational forces and/or linear forces). In addition to establishing a single maximum threshold over which the risk of a concussion is high, the impact thresholds may include a series-based threshold that takes into account a series of impact events over a certain period of time. The series-based threshold would indicate the risk of concussion due to a series of smaller impact forces (relative to the single maximum threshold) encountered over a period of time. For example, the series-based threshold can be based on a weighted average of the hits, wherein the threshold (as measured by the weighted average) is reduced based on the number of hits. The rate of change in the reduced threshold force may be linear or exponential. These series-based thresholds are a form of dynamic thresholds, in that they change during a session (e.g., a game) of the user's activity, or over multiple sessions of activities. It should be understood that the user's prior concussion history (both short term, such as the impacts occurring over a 24-hour period, or long term, such as a prior concussion within the last two months) is also biometric data of the user that can be used to establish the thresholds. These different initial thresholds values and dynamic threshold values for the user may be stored in various look-up tables in the memory of the PCBA 2 within the mouth guard 1. And, as discussed below in FIG. 8, they may be modified over the course of operation of the mouth guard 1 by the smart device 50.

The user can also indicate different activities for which he or she intends to use the mouth guard 1. For example, a user may indicate that she intends to use the mouth guard for boxing and soccer. Each of these activities may have different impact threshold data that will be stored on the memory device of the PCBA 2 due to the different types of impact forces and frequency of impact forces that are anticipated. Some of the differences may be due to the sensitivity of the impact forces to be detected by the sensors on the PCBA 2. As one example, boxing may have hits that are longer in duration due to the deformation of the boxing gloves, whereas an undesirable head-to-head impact in a soccer match can be of very short duration. Additionally, boxing regulations may restrict certain hits, such as a hit to the back of the head. Because the mouth guard 1 can sense the directionality of hits, a hit to the back of the head in a boxing match, regardless of force, may cause the LED 10 to activate to inform the boxers (and referee) that a restricted hit occurred. Accordingly, the inventive mouth guard 1 may include impact threshold data (e.g., different look-up tables) for multiple activities of the user. The user would use a smart device (e.g., mobile phone 50 in FIG. 8) to communicate the specific activity chosen for that particular day (or session) to the mouth guard 1 via the Bluetooth connection. The processor 28 then pulls the corresponding impact threshold data stored within the memory device for the user's chosen activity and uses that impact threshold data for comparisons during the activity. It should be noted, as explained above, that two different users participating in the same two activities will still have different impact threshold data for each activity (e.g., boxing look-up table #1, soccer look-up table #1, boxing look-up table #2, soccer look-up table #2,) because of their different biometric information. Accordingly, the user's indication of his or her activity or activities (not just biometric information) may also dictate the types of impact force threshold data that are stored in the memory of the PCBA 2.

The various impact thresholds for the user and potentially other data useful for determining concussion risk can be uploaded to one of the memory devices via the SWD debug port 18. Of course, the SWD debug port 18 can be used to upload other data and software into the memory 34. Once the necessary information is loaded on the PCBA 2 and final programming is complete, the SWD debug port 18 can be removed via perforations 19 before it is encased within the flexible material of the mouth guard 1.

Because the high-G accelerometer 30 detects directional impact data, it is preferably located in a predictable reference point and, therefore, is mounted within the center tab 11 such that it is adjacent to the midline of the user's top incisors. Because its physical structure is molded into the mouth guard 1 as discussed below in FIG. 6, the high-G accelerometer 30 maintains this same position along the centerline near the biting or incisive edge line of a maxillary central incisors. In some embodiments with a user having an abnormal, or untraditional, mouth structure regarding tooth placement, fillers may be used in the mouth guard 1 to fill in gaps between teeth (for instance additional material to compensate for missing teeth, misplaced teeth, etc.). Preferably, the electrical components and, in particular, the sensors (e.g., high-G accelerometer 30, magnetometer 31, and gyroscope 32) maintain direct contact with the structure of the mouth guard 1, which, in turn, is molded to maintain direct contact with the skeletal structure and teeth of the head. As such, the sensors maintain indirect (but rigid) contact with the skeletal structure of the head. The sensors can also detect the movement and forces associated with the mouth guard 1 being dropped from the player's mouth or hand so as to discount such impact forces.

An LED driver 9 controls the actuation of an LED 10 on the front side 4 of the PCBA 2. The LED 10 is used to indicate to others (e.g., other players, a coach, a referee) that the user has experienced a certain concussion-risk event (or events when considering a series of impact forces over a period of time). The LED 10 can also indicate operation (i.e., on/off), battery-charge life, malfunction, etc. The LED driver 9 is located on front side 4 of PCBA 2 so that it can be viewed between the user's lips. In a preferred embodiment, the LED driver 9 controls both the light intensity and the color of the LED 10 via the current driven into LED 10. By supplying a fixed current, the LED driver 9 can modify that current to get the appropriate pattern of light(s) displayed on the LED 10 to indicate certain information to others located around the user (and to the user when he or she removes the mouth guard 1 from his or her mouth).

The battery 22 typically supplies between 3 volts and 4.2 volts. To maintain adequate performance levels of components, a main voltage converter 26 is used to provide a constant voltage to the components. A battery charger 23, which is coupled to the wireless charging receiver 20, preferably includes an integrated circuit to monitor and provide a specific charging profile for the battery 22. The wireless coil 21 receives alternating current, and converts it to direct current for the battery 22. The wireless coil 21 preferably receives alternating current at approximately one million hertz, or as otherwise known in the art.

The PCBA 2 includes a battery fuel gauge 24 near one of the end portions 3. The battery fuel gauge 24 utilizes a Coloumb-countering feature and a comparative table to calibrate the charge remaining on the battery 22. The battery 22 typically operates in multiple modes, such as in a normal operational mode, a charging mode, and a standby mode. The battery 22 is preferably a Lithium polymer battery with a low-profile and an ability to slightly bend during the manufacturing process (discussed in FIG. 6) to foster an ergonomic fit into the mouth guard 1. In one preferred embodiment, a gel electrolyte lithium battery is preferred, which most preferably uses a non-toxic electrolyte. While lithium polymer batteries are preferred, as battery technology improves and/or changes, other types of batteries having a thin profile and a light weight (and preferably the non-toxic nature of the electrolyte) will drive selection of battery. A battery protection component 27 may be used to prevent shorting of the battery via overcharging and/or undercharging. The battery protection 27 also prevents the battery 22 from running below a minimum charge. Because of the size of the battery 22 (length and height dimensions), the battery 22 is located toward one of the end portions 3 of the PCBA 2 in which there is more space between the buccal surface and the bone/teeth. Advantageously, the mouth guard 1 has a larger radius of curvature in this region as well, which results in less bending of the battery 22.

The PCBA 2 includes a wearer notification component 36, preferably adjacent to the end 3 of the PCBA 2. The notification component 36 uses electrical energy to generate mechanical energy to provide a haptic feedback, a vibratory feedback (e.g., a buzzer), or an auditory feedback, which may be both heard by the ear and felt within the mouth. The notification component 26 may include magnetics and/or piezoelectric elements. Because of the generation of mechanical and/or audible energy, the notification component 36 may be one of the high-energy consumption components on the PCBA 2 (the LED 10 is often the highest energy consuming component, depending on the size and functionality). Furthermore, the notification component 36 typically has the tallest profile rising from the PCBA 2 and uses a fair amount of three-dimensional space extending off of the surface of the PCBA 2. To create the most space for the notification component 36, the notification component 36 is located toward the end portion 3 of the PCBA 2 in which there is more space between the buccal surface and the bone/teeth. The notification component 36 is preferably positioned on the back side 6 of the PCBA 2 directly adjacent to the bone just below the maxillary sinus cavity to vibrate the bone and conduct vibrations along the maxilla toward the ear, which may provide a tonal sensation and/or an audible sensation (depending on the vibration frequency).

In other embodiments, the notification component 36 may use an air vibration conductor via a magnet and plate using compressed air. Alternatively, the notification component 36 may create haptic feedback through motors using offsetting weights. Alternatively, the notification component 36 may include a linear resonant actuator (LRA) using a small metal block, or pin.

The notification component 36 is particularly useful to notify the user that he or she has received a significant impact (or series of impacts) that he or she may not have recognized. For example, after a single, high-force impact creates a substantial risk of concussion, the processor 28 receives the data from the rotational and/or linear force sensing units and determines whether the predetermined threshold has been exceeded. If so, the processor 28 then communicates with the notification component 36 to begin activation that results in the haptic feedback, a vibratory feedback (e.g., a buzzer), or auditory feedback. In some embodiments, the processor 28 may delay the activation of the feedback by a set period of time (e.g., 10 or 20 seconds) such that the user has some time to regain full awareness after a big hit, so as to understand what the feedback is intended to mean. The notification component 36 can also provide different types of feedback (in duration, magnitude, or frequency) to inform the user of different events. For example, a series of lesser hits within a period of time that causes the series-based threshold to be exceeded may have a different feedback (e.g., smaller magnitude and a lower frequency) than a single, high-force impact of the component (e.g., high magnitude and a high frequency, or constant feedback). The notification component 36 can also communicate other events, such as a low-battery mode or to remind the user that system is operational, which may be accomplished in a single subtle feedback at a very low frequency (e.g., every 60 seconds).

As seen in FIGS. 1 and 2, the vast majority of the components electronics are within the middle portion 7 of the PCBA 2, but most are to the side of center tab 11 except for the LED 10 and the high-G accelerometer 30. Further, the vast majority of the sensitive electrical components are on the back side 6 of the PCBA to allow them to be impressed into the flexible material of the mouth guard 1 in a direction that faces the teeth to give them added protection from impacts to the face. As noted above, the LED 10 is on the front side 4 so as to permit the viewing of the LED 10 by other people around the user. The battery 22 is likewise on the front side 4 of the PCBA 2 for spatial reasons. The charging coil 21 is on the front side 4 to provide better access for charging the battery 22. FIGS. 1-2 represents one embodiment of the present invention and the components can be rearranged on the PCBA 2.

The width of the of the PCBA 2 (top-to-bottom) varies along the length and is between 2 mm and 15 mm, with the largest width being in the end region 3 in the illustrated embodiment. The middle portion 7 has a height in the range of 6 mm to 15 mm, and is preferably about 12 mm. Each of the end portions 3 having a width in the range of 8 mm to 15 mm. The bridge portions 16, 17 have a width that is smaller than 40% (and preferably smaller than 30%) of the widths of the end portions 3. The bridge portions 16, 17 have a width that is smaller than 50% (and preferably smaller than 40%) of the width of the middle portion 7.

Figure 3:
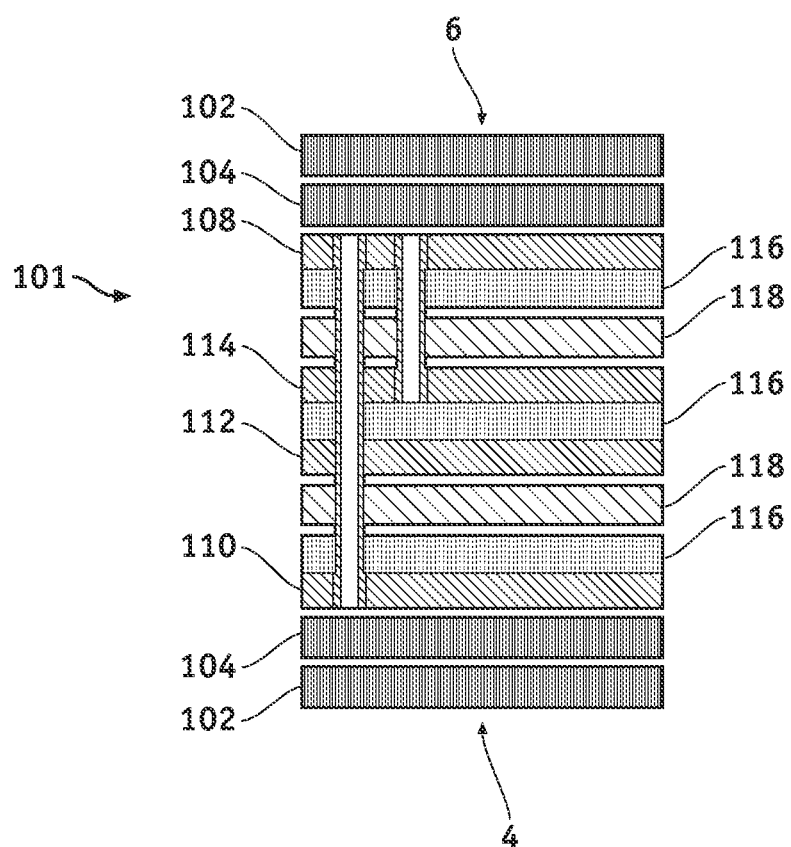
FIG. 3 illustrates one embodiment of a cross-sectional view of the printed circuit board used in the flexible printed circuit board assembly of FIG. 1.

FIG. 3 is a general schematic in cross-section of one preferred embodiment for a flexible printed circuit board (PCB) 101 that would receive the electrical components and form the PCBA 2. All layers are shown in FIG. 3, though not all of them are present across the entire PCB 101 as understood by those skilled in the art. Unlike prior art rigid PCBs that include foil stacked on glass or other rigid materials, the flexible PCB 101 is preferred as its shape may be modified and bent into an ergonomic position, as discussed more in FIG. 6. The flexible PCB 101 has multiple conductive layers, such as four metallic traces, that transit the signals between the electrical components. An upper and lower overlay surfaces 102 protect those internal layers, but would not present in areas when component soldering is required. Two solder-resist layers 104 are located on the metallic (e.g. copper) trace 108 of the back side 6 (primary component side) and the metallic trace 110 on the front side 4, at least in regions of the PCB 101 where component soldering is needed. The electrical working layers further include a ground layer 112 and a power layer 114 (or signal and power layer 114). Each of the four metal layers 108, 110, 112, and 114 is about 0.02 mm in thickness (e.g., 0.018 mm or 0.022 mm).

The ground layer 112 and the power layer 114 is separated by a dielectric layer 116, such as polyimide. The back side copper trace 108 is separated from the power layer 114 by a dielectric layer 116 and an adhesive layer 118. The front side copper trace 110 is also separated from the ground layer 112 by a dielectric layer 116 and an adhesive layer 118. The dielectric layers 116 and adhesive layers 118 are each about 0.025 mm in thickness. The overall thickness of the PCB 101 is between about 0.2 mm and about 0.3 mm. The PCB 101 may include exterior side tape on both the front side 4 and back side 6 in some regions, which is useful in mechanically attaching some of the larger components (e.g., the battery 22 and the charging coil 21) to the PCB 101.

FIGS. 4A and 4B illustrate the left side and right side cross-sections of the PCBA 2 along, respectively, lines 4A-4A and lines 4B-4B of FIG. 1, both of which cut through the high-G accelerometer 30 on the back side 6 and the LED 10 on the front side 4. The dimension X-X refers to the overall thickness of the printed circuit board, which is about 0.2 mm in the illustrated embodiment. The dimension Z-Z in FIG. 4A references the height of the LED 10, which is about 0.6 mm. The battery 22 shown in FIG. 4B has a height dimension W of about 2.0 mm. The notification component 36 shown in FIG. 4B also has a height dimension U of about 2.0 mm. The charging coil 21 shown in FIG. 4A has a height dimension of about 0.4 mm, which is less than the height dimension of the LED 10. One of the parts of the coil charging receiver 20 has a height dimension Y-Y in FIG. 4 of about 1.2 mm. According, while the overall PCBA 2 has a length of about 110 mm, the maximum overall height dimension of the PCBA 2 (including components on the top side 4 and read side 6) is less than 5 mm in all regions, such that the ratio of length to overall height is greater than 20.

The end portion 3 with the battery 22 and notification component 36 may have a maximum overall height dimension of about 4.2 mm, and is preferably less than 4 mm. In the middle portion 7, the maximum overall height dimension at any point along the length is less than 2 mm (e.g., 1.8 mm), and is preferably less than 1.5 mm, which is dictated by the nearly overlaying the high-G accelerometer 30 on the back side 6 and the LED 10 on the front side 4. In the end portion 2 with the coil 21, the maximum overall height dimension is less than 2 mm (e.g., 1.9 mm), and is preferably less than 1.5 mm. The bridge portions 16, 17 of the PCBA 2 that connect the end portions 3 and the middle portion 7 preferably include no components and have a maximum dimension between about 0.2 mm to 0.3 mm, and preferably about 0.2 mm (i.e., the thickness of the printed circuit board in FIG. 3) to provide additional flexibility (both bendability and rotational twistability) to the overall PCBA 2, which is helpful when manufacturing mouth guard 1 as shown in FIG. 6. FIGS. 4A and 4B illustrate only one exemplary preferred embodiment of a low-profile PCBA 2 for use in the mouth guard 1, as other component arrangements and configurations can be used.

Figure 5:
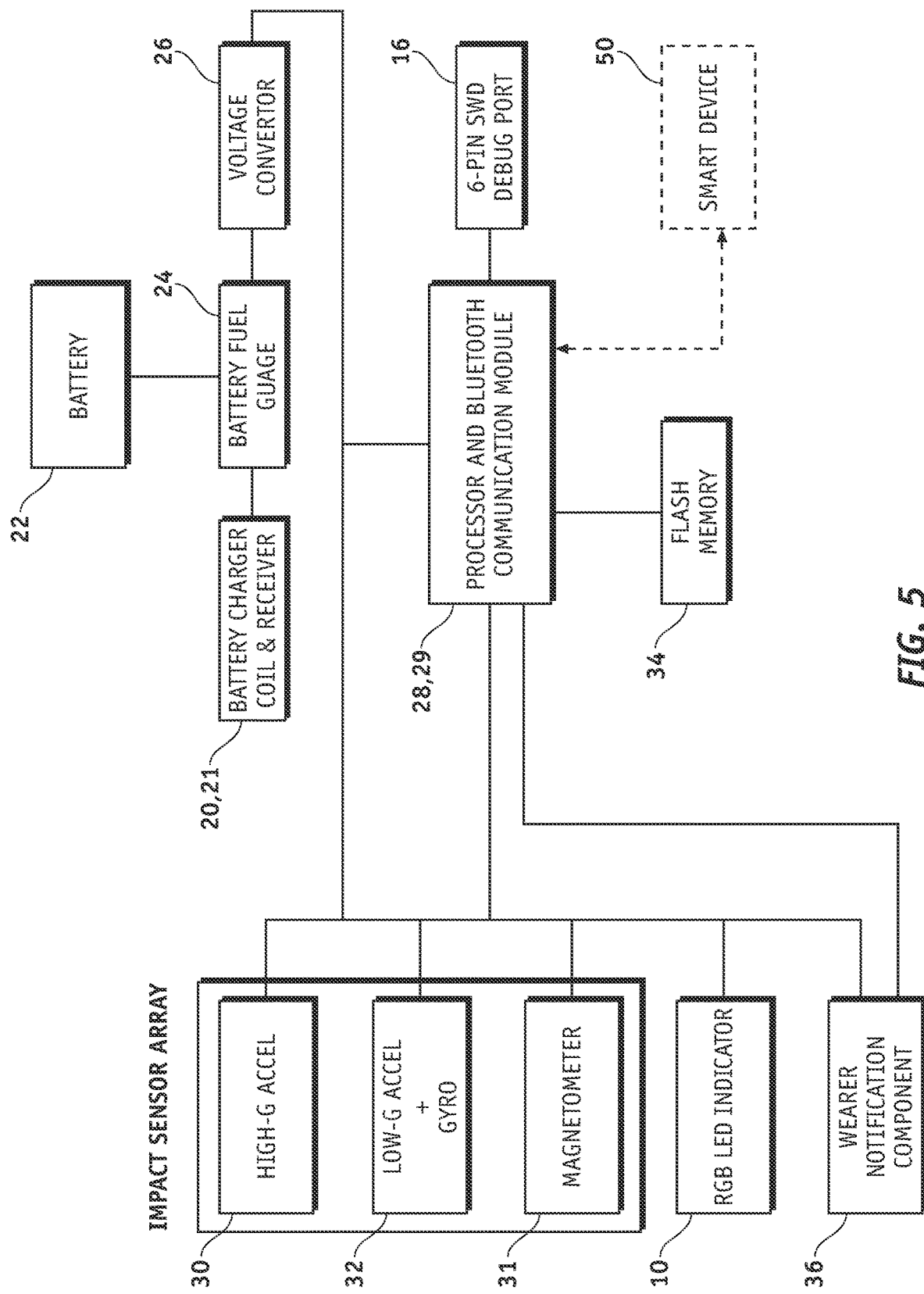
FIG. 5 illustrates a schematic of the components of the flexible printed circuit board assembly of FIG. 1 according to one embodiment.
Figure 8:
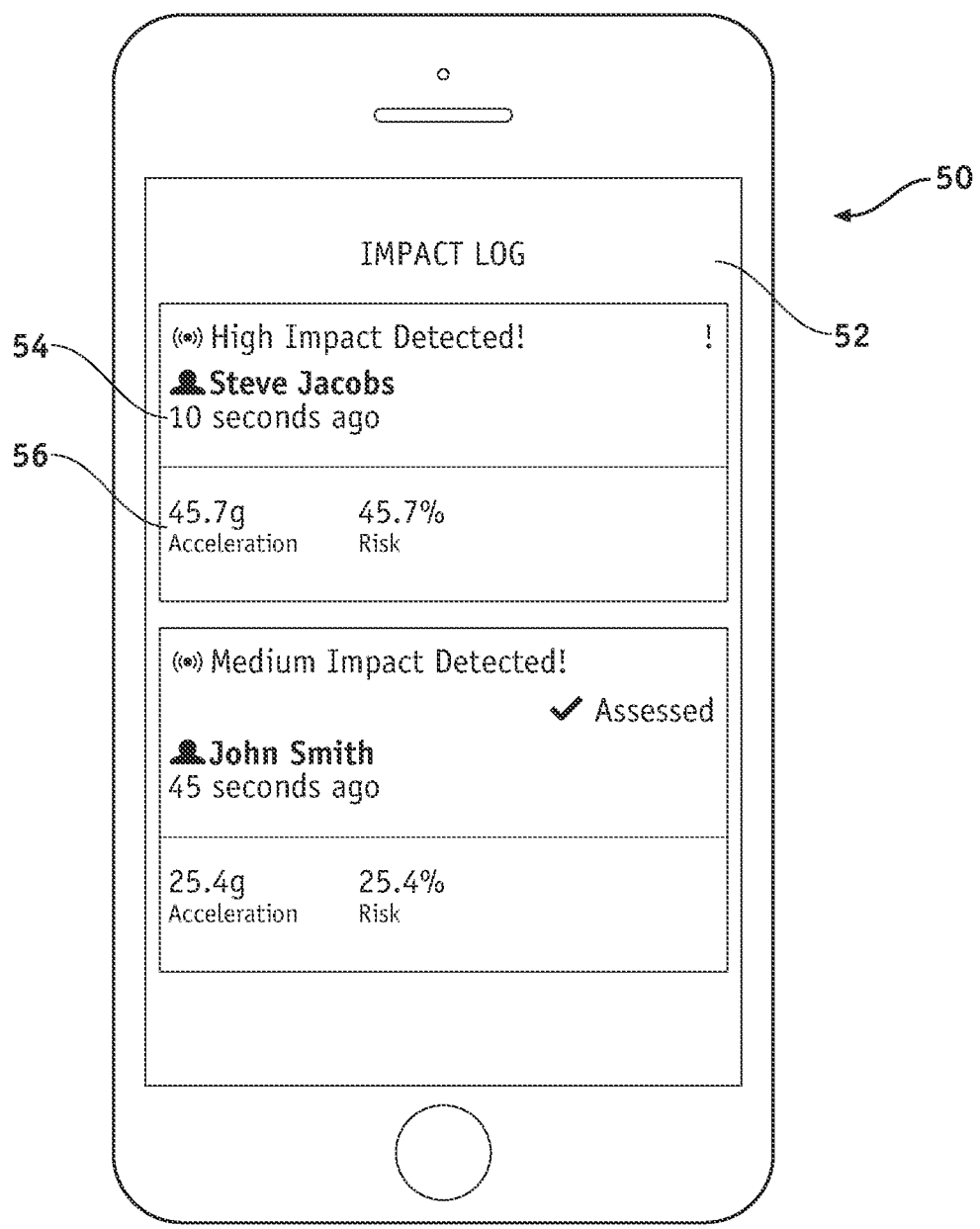
FIG. 8 illustrates a graphical user interface on a mobile device that provides an indication of impacts for multiple users of the mouth guard.

FIG. 5 is one embodiment of a general schematic illustrating the connectivity of the components mounted on the PCBA 2. The battery 22 provides power to all of the various components. The processor module includes the main processor 28 in communication with the components, receiving data (e.g., from the sensors) and sending communications instructions (e.g., to the LED 10 and notification component 36). The processor module may also contain the Bluetooth transceiver 29 that allows for communication with one or more external devices, such as the smart device 50 associated with of the user, a parent, a coach, a referee, etc. The smart device 50 would include the software (e.g., in the form of an app) to receive and transmit information with the Bluetooth transceiver 29 within the mouth guard 1 while in use or before/after use. The smart device 50 also provides remote storage, computation, and display of risk factors associated with one or more mouth guard devices. The smart device 50 may be smart phone, a tablet, or a computer. One exemplary smart device 50 is shown in FIG. 8. Other system configurations for the connectivity of the components of the PCBA 2 are possible as well.

FIGS. 6A-6D illustrate a series of stages in developing the mouth guard 1. A model 80 of the user's mouth, specifically of the maxillary region teeth, is made. The model 80 may be created by a dental professional, by use of an intra-oral scanner, or by use of a simple home impression tray. As showing in FIGS. 6A-6D, the model 80 is a stone model that is formed within an impression that was impressed over the user's teeth and gingiva. The stone is poured into the impression to create the stone model 80, resulting in a replica of the user's upper teeth and bone structure.

Figure 6A:
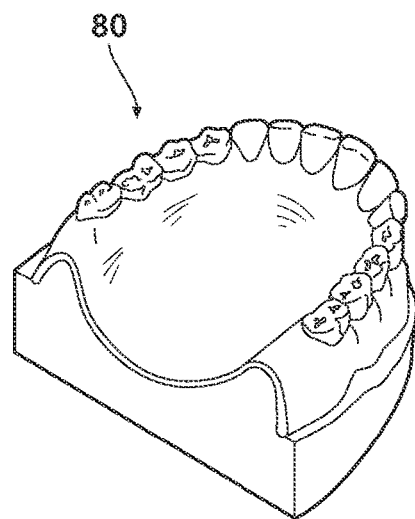
FIG. 6A illustrates a user's stone model that replicates his or her maxillary region and associated dentition, which is used in the process of manufacturing the inventive mouth guard.
Figure 6B:
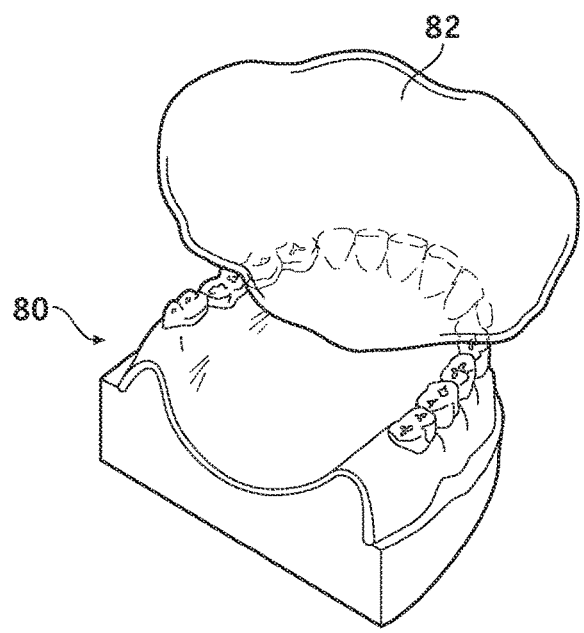
FIG. 6B illustrates overlaying a first layer over the user's stone model in the process of manufacturing the mouth guard.

In one preferred embodiment shown in FIGS. 6A-6D, the method for forming the wearable mouth guard 1 is performed as follows. As shown in FIG. 6A, the model 80 is placed upside down and inserted into a thermoforming machine (e.g., a pressure thermoforming machine) that is designed to produce custom mouth guards, such as a Drufomat® manufactured and sold by Dentsply Sirona. As shown in FIG. 6B, a first base layer 82 of about 3 mm of EVA thermoplastic (other flexible materials are possible as well) is placed over the model 80. Within the thermoforming machine, the first layer 82 is heated and thermoformed over the model 80 so that it will substantially conform to the anatomical structures (e.g., bone, gingiva, teeth, etc.) of the maxillary region of the oral cavity of user, as dictated by the model 80. Due to the heat and pressure, the initial thickness of the first layer 82 decreases by about 30% to 40% when overlaid onto the model 80. For example, when the first layer 82 of 3 mm is used, the final thickness of the first layer 82 is approximately 1.8 mm to 2.1 mm. The first layer 82 is then ready to receive the PCBA 2. It should be noted that trimming and polishing may be performed on the first layer 82, as necessary.

The PCBA 2 is tested and programmed prior to being molded into the base layer 82. Once the PCBA 2 passes all tests and the latest firmware has been programmed, the region with the SWD debug port 18 (FIGS. 1-2) is trimmed off using scissors along the perforations 19. By use of the debug port 18, the memory 34 is programmed to include, for example, the specific predetermined threshold data points based on the biometric information received from that particular user.

Once the programmed PCBA 2 is ready, a heat gun is employed to sweep across and soften the first layer 82. In one embodiment, a 700 W heat gun with about 120 L/m of air flow is set to 350° C. and is used for about 30 seconds to heat the material. With the first layer 82 now softened, the PCBA 2 is placed with the back side 6 (and the majority of the electrical components) facing inward towards the softened first layer 82. The softening is not harsh enough to affect the conformance of the first layer 82 to the underlying model 80. For the first connection point, the high-G accelerometer 30 on the central tab 11 (not shown in FIG. 6) is positioned directly adjacent to the midline of the two central incisors. The central tab 11 and physical structures of the high-G accelerometer 30 and adjacent components, such as the LED driver 9 and the processor 28, on the rear side 6, are forced into and depressed within the first layer 82. For vertical alignment, the edge of the middle portion 7 closest to the LED 10 should be aligned with the cutting edges of the replica incisors within the model 80. Next, the remainder of the components on the rear side 6 of the middle portion 7 are impressed into the softened first layer 82.

Figure 6C:
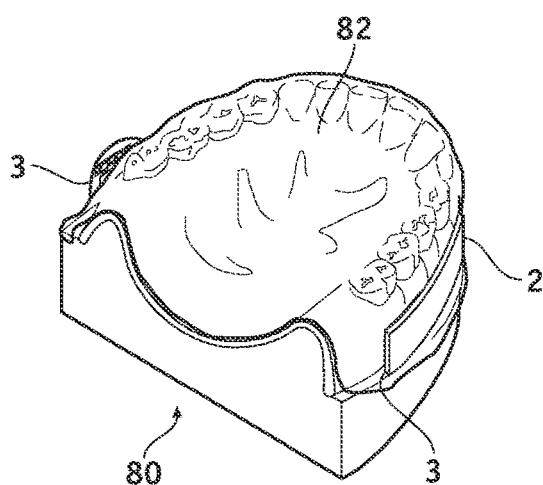
FIG. 6C illustrates embedding the flexible printed circuit board assembly of FIGS. 1-2 in the first layer that overlays the user's stone model in the process of manufacturing the mouth guard.

After the components of the middle portion 7 are impressed within the first layer 82, the remaining portions of the left side and right side of the PCBA 2 are depressed into the first layer 82, including all components (e.g., wireless charging components 20 and the notification component 36) near the two end portions 3. Typically, the heat gun may be needed again to soften the first layer 82 along its sides to accommodate those materials. The bridge portions 16, 17 of the PCBA 2 provide the bending and twisting needed to accommodate the wide variety of anatomic variations in the maxilla region of the general population. As shown in FIG. 6C, the PCBA 2 is fixed into the first layer 82 by impressing the geometric arrangement of the electrical components on the back side 6 of the PCBA 2 into the softened first layer 82. The LED 10, the battery 21, and the charging coil 21 are mounted to the front side 4 of the PCBA 2 and, thus, project outwardly away from the underlying model 80.

Because of the unique shape of the model 80 due to each user's unique anatomy, the PCBA 2 will fit a bit differently on the first layer 82 for each user. Accordingly, a deformable filler material, such as Fillin™ from Dreve Dentamid GmbH, is provided to fill in the small gaps between the back side 6 of the PCBA 2 and the first layer 82, and also between the first layer 82 and some of the larger inwardly-facing (tooth-facing) components, such as the wireless charging components 20 and the notification component 36. This deformable material is similar to a wax such that it can be rolled into thin pieces and shaped as necessary. Additionally, the deformable filler material is used to smooth any rough surfaces (like the corners of the battery 22 or the coil 21) to prevent unnecessary pressure points for the next layer. This helps to eliminate gaps between the PCBA 2 (and the fronts-side electrical components) and the base layer 82, which may permit air to become trapped when the second layer 84 (e.g. EVA) is applied. In other words, the deformable filler material is used to fill in gaps and smoothen sharp corners for a more reliable placement of the second layer 84. The deformable filler material can also be type of hot glue, such as EVA.

Figure 6D:
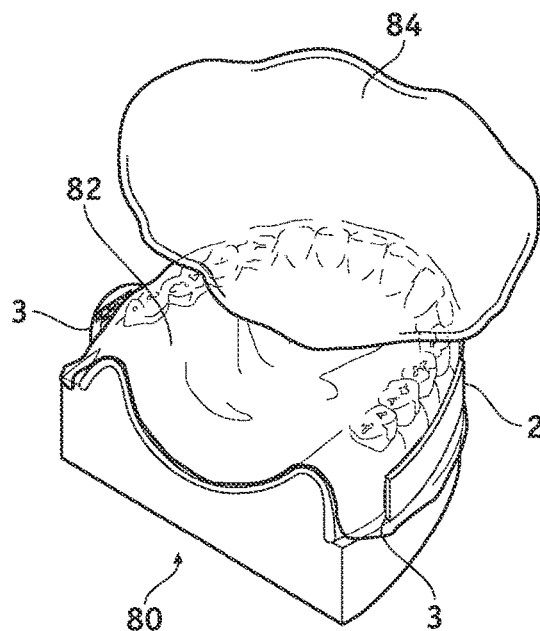
FIG. 6D illustrates overlaying a second layer over the first layer and the embedded flexible printed circuit board assembly in the process of manufacturing the mouth guard.

As shown in FIG. 6D, the second layer 84 is placed over the combination of the first layer 82 and the PCBA 2 (and any Fillin™ material) within the thermoforming machine, to allow pressure molding of the second layer 84 over the PCBA 2. The heated second layer 84 is formed to fit over the LED 10, the battery 22, and the charging coil 21 on the front side 4 of the PCBA 2. The second layer 84 can be anywhere from 1 mm to 4 mm and, like the first layer 82, becomes thinner (and denser) upon application of heat and pressure. Assuming a 2 mm final thickness of the first layer 82, a second layer 84 of 1 mm creates about 3-4 mm thickness across most of the mouth guard 1, which may be more appropriate for sports like biking, basketball, etc. Assuming a 2 mm final thickness of the first layer 82, a second layer 84 of 4 mm creates about a 4-5 mm thickness across most of the mouth guard 1, which may be more appropriate for direct impact sports, such as boxing or football. The thickness of the second layer 84 depends in part on user preference, and the requirement for safe functionality. Trimming and polishing can be performed after the second layer 84 has been added to the first layer 82 and PCBA 2.

The total thickness, of course, varies a bit over the regions of the mouth guard 1 due to the electrical components on the PCBA 2. For example, in the front portion 92 (FIG. 7) of the mouth guard 1 having an arch-shaped surface 94 (FIG. 7) exposed to the buccal surface, the end portion 3 of the PCBA 2 having the battery 22 and notification component 36 will have the greatest localized thickness of the overall mouth guard 1, with a thickness less than 7 mm, and preferably less than 6 mm. In the front portion 92 of the mouth guard 1 exposed to the buccal surface and near the middle portion 7 of the PCBA 2 (with the majority of the components), the maximum localized thickness of the mouth guard 1 will be less than 5 mm, preferably less than 4 mm. In the front portion 92 of the mouth guard 1 exposed to the buccal surface near the other end portion 3 of the PCBA 2 having the charging coil 21 and wireless charging components 20, the maximum localized thickness of the mouth guard 1 will be less than 5 mm, preferably less than 4 mm. Between these three regions, the thickness in the bridge portions 16, 17 be less than 4 mm, or less than 3 mm.

In one example illustrating the thickness of the front portion 92 of the mouth guard 1 that faces the buccal region of the user's mouth, with the first layer 82 being 3 mm in thickness and the second layer 84 being 2 mm in thickness, the end portion 3 with the battery 22 has a maximum thickness of about 5.5 mm, the middle portion 7 has a maximum thickness of about 3.0 mm, and the end portion 3 with the charging coil 21 has a maximum thickness of about 3.3 mm. In a second example illustrating the thickness of the front portion 92 of the mouth guard 1, with the first layer 82 being 3 mm in thickness and the second layer 84 being 3 mm in thickness, the end portion 3 with the battery 22 has a maximum thickness of about 6.1 mm, the middle portion 7 has a maximum thickness of about 3.7 mm, and the end portion 3 with the charging coil 21 has a maximum thickness of about 4.0 mm The overall thickness of the mouth guard 1 should not necessarily impact the data measured, but can be compensated for by algorithms or software when programming the processor 28 for the predetermined threshold levels. For example, when additional thickness of the mouth guard 1 is used, it dampens the measured impact force. In other words, the mouth guard 1 is effectively reducing the amount of impact/force on the skull and brain by a small amount.

FIG. 7 demonstrates the finished mouth guard 1 produced by the manufacturing process of FIG. 6. The mouth guard 1 includes a main body having the arched-shaped peripheral side surface 90 on its front portion 92 that generally follows the contour of the user's dental arch in the maxilla region. The front portion 92, which is comprised of the layering of the first layer 82, the PCBA 2, and the second layer 84, includes the electronic components. While most of those electronic components are facing inwardly toward the teeth (and not seen in FIG. 7), but the LED 10 faces the buccal direction and can be seen through the second layer 84 of plastic. The charging coil 21 is also seen on the front side 4 of the PCBA 2. The center tab 11 that receives the high-G accelerometer 30 is positioned in a location that is substantially aligned with the midline of the upper incisors of the user. The mouth guard includes an arch-shaped depressed portion 94 connected to the front portion 92 that is sized and shaped to receive teeth of the user to help retain the mouth guard in a fixed position in the mouth. A palate portion 96 of the mouth guard 1 engages the roof of the mouth. Given the drive to produce a device that minimizes the size, permits accurate data collection, and provides user comfort, the mouth guard 1 of the present invention works better with the aforementioned forming process. Though it is possible to use a mouth guard created from a one-size-fits-all approach (such as boil-and-bite mouth guards) with the present invention, the aforementioned forming process is the preferred method of manufacturing.

The first layer 82 can be made of a clear or colored material. The second layer 84 is preferably clear in the region of the LED 10 so that it can be observed by others, but other regions of the second layer 84 can be colored. If no LED 10 is present in the mouth guard 1, then both layers 82 and 84 can be colored and opaque.

As shown in FIG. 8, a remote receiver in the smart device 50 may act with a local app (e.g., software application) to receive and display real-time data or information from the mouth guard(s) 1 via the communication system (e.g., Bluetooth transceiver 29). Preferably, the remote smart device 50 includes a display 52 that permits the displaying of certain types of impact information from a specific mouth guard 1 associated with a user (or multiple mouth guards from several users). For example, the display 52 may include a relative time indicator 54 that may demonstrate the timing of a recent impact event. Furthermore, the display 52 may include impact data 56, such as acceleration and force (linear and/or rotational). Further, a risk calculation 58 may be displayed. The risk calculation may be determined either locally or remotely, and is based predetermined impact thresholds unique to each user based on his or her biometric information. The risk calculation can also be dynamically generated in that it is based on series of impacts within a certain period of time. Accordingly, the present invention contemplates that when the mouth guard 1 senses a force exceeding a certain threshold, there are multiple options for notifications: (i) to the user via the feedback from the notification component 36, (ii) to other individuals near the user via the LED 10, and (iii) to more-remotely situated individuals via the display 52 of the smart device 50.

As noted above, the smart device 50 also permits the user to communicate with the mouth guard 1. For example, the user can use the smart device 50 to select his or her activity for the day such that processor 28 then selects the corresponding impact force threshold data for that particular activity. The user can use the smart device 50 to indicate the occurrence of a prior concussion, such that processor 28 then selects a reduced impact threshold data. Or, in another alternative, the user can dictate the reduced value of the impact threshold by indicating a specific percent reduction in the threshold if he or she desires to be notified of lesser hits to stay far away from injury. The smart device 50 may, in response to the user's command, download force data from memory 34 on the PCBA 2, and then send instruction to erase the prior force data or segments of the prior force data.

The smart device 50 is preferably in communication with a remote storage (e.g., the cloud) that contains the various types of threshold data for all users or a subset of users (e.g., football players). As better and more precise threshold data is learned and stored in the remote storage, the smart device 50 downloads that updated data, which can then be transmitted to the user's mouth guard 1 via the Bluetooth connection. In another example, if the user decides to try another activity, such as rugby, the smart device 50 can download the rugby threshold data from the remote storage and then transmit that rugby threshold data to the customized mouth guard 1 for that user.

These embodiments and obvious variations thereof is contemplated as falling within the spirit and scope of the claimed invention, which is set forth in the following claims. Moreover, the present concepts expressly include any and all combinations and subcombinations of the preceding elements and aspects.

We claim:

1. A method for manufacturing a custom mouth guard that detects impact forces of a user, comprising:
conforming a first layer of material to a model of the user's maxillary region, the model includes the user's replicated teeth;
placing a flexible printed circuit board onto the first layer, the flexible printed circuit having a first end portion located adjacent to one molar region on the replicated teeth, a second end portion located adjacent to the other molar region on the replicated teeth, a middle portion adjacent to an incisor region on the replicated teeth, and at least one bridge portion adjacent to one of the first and second end portions, the first and second end portions having widths that are greater than the at least one bridge portion, the flexible printed circuit having a plurality of components including at least a processor, a memory device, a first sensor for determining linear acceleration, a second sensor for determining rotational acceleration, a battery, a wireless battery charging component, and a communication transmitter for transmitting an indication signal in response to an impact experienced by the user, the battery being mounted in the first or second end portions of the printed circuit board, the wireless battery charging component being mounted in the first or second end portions of the printed circuit board, the communication transmitter being mounted in the middle portion of the printed circuit board, wherein the placing includes (i) initially forcing one of the components into the first layer at a location aligned with a central part of the incisor region to set the location for the printed circuit board and (ii) subsequently forcing other components into the first layer at locations closer to the molar regions;
overlaying a second layer of material over the flexible printed circuit board and the first layer;
heating at least one of the first and second layers to help conform the plurality of components on the flexible circuit board to the first and second layers of material to create the custom mouth guard, the custom mouth guard having a front portion with a generally arched-shaped peripheral side surface for facing the buccal region of a mouth of a user, the printed circuit board being within the front portion of the custom mouth guard, the wireless battery charging component and the communication transmitter facing outwardly toward the buccal region.

2. The method of claim 1, wherein the act of heating occurs though a pressure thermoforming machine.

3. The method of claim 1, further including, after overlaying the second layer, trimming or polishing the overall structure to create the final custom mouth guard.

4. The method of claim 1, further including, before overlaying the second layer of material, adding deformable material along sides of the components mounted on the flexible printed circuit board.

5. The method of claim 1, wherein the maximum thickness of the front portion is less than 7 mm.

6. The method of claim 1, wherein the front portion of the custom mouth guard includes a central section for being adjacent to the central incisors, the linear and rotational acceleration sensors being mounted on the middle portion of the flexible printed circuit board that is positioned within the central section.

7. The method of claim 1, wherein the at least one bridge portion includes two bridge portions, the two bridge portions connecting the first and second end portions to the middle portion.

8. The method of claim 1, further storing impact threshold data on the memory device on the flexible printed circuit board, the impact threshold data being based on biometric information associated with the user.

9. The method of claim 8, wherein the biometric information includes at least age, sex, and weight.

10. The method of claim 1, wherein the model is a stone model taken from an impression of the user's maxillary region.

11. The method of claim 1, wherein the model is a created from an intra-oral scan of the user's maxillary region.

12. A method for manufacturing a custom mouth guard that detects impact forces of a user, comprising:
receiving a model of the user's maxillary region that includes replicated teeth;
storing impact threshold data on a memory device of a flexible printed circuit board, the flexible printed circuit board having a plurality of components including at least a processor, the memory device, a first sensor for determining linear acceleration, a second sensor for determining rotational acceleration, a battery, a wireless battery charging component, and a communication transmitter for transmitting an indication signal in response to an impact experienced by the user;
after the receiving and the storing, conforming a first layer of material to the model of the user's maxillary region;
forcing the flexible printed circuit board into the first layer to impress the flexible printed circuit board into the first layer; and
conforming the second layer of material to exposed surfaces of the flexible printed circuit board and the first layer to create the custom mouth guard, the custom mouth guard having a first molar region, a second molar region, and an incisor region, the flexible printed circuit having a first end portion located within the first molar region of the custom mouth guard, a second end portion located within the second molar region of the custom mouth guard, a middle portion located within the incisor region of the custom mouth guard, the first and second end portions having widths that are greater than the middle portion, the battery being mounted in the first or second end portions of the printed circuit board, the wireless battery charging component being mounted in the first or second end portions of the printed circuit board, the communication transmitter being mounted in the middle portion of the printed circuit board.

13. The method of claim 12, wherein both acts of conforming occur though a pressure thermoforming machine.

14. The method of claim 12, further including, receiving biometric information associated with the user, the biometric information including at least age, sex, and weight, the impact threshold data being based on the biometric information.

15. The method of claim 12, further including, after the storing, removing a port section from the flexible printed circuit board to reduce an overall size of the flexible printed circuit board.

16. The method of claim 12, wherein the middle portion of the flexible printed circuit board has a length that is between about 25% and 50% of the overall length of the flexible printed circuit board, the middle portion including two cut-outs to enhance the bendability of the flexible printed circuit board.

17. The method of claim 12, wherein the model is a stone model taken from an impression of the user's maxillary region.

18. The method of claim 12, wherein the model is a created from an intra-oral scan of the user's maxillary region.

19. The method of claim 12, further including, before confirming the second layer of material, adding deformable material along sides of the components mounted on the flexible printed circuit board.

20. A method for manufacturing a custom mouth guard that detects impact forces of a user, comprising:
 conforming a first layer of material to a model of the user's maxillary region, the model includes the user's replicated teeth;
 placing a flexible printed circuit board onto the first layer, the flexible printed circuit having a first end portion located adjacent to one molar region on the replicated teeth, a second end portion located adjacent to the other molar region on the replicated teeth, a middle portion adjacent to an incisor region on the replicated teeth, and at least one bridge portion adjacent to one of the first and second end portions, the first and second end portions having widths that are greater than the at least one bridge portion, the flexible printed circuit having a plurality of components including at least a processor, a memory device, a first sensor for determining linear acceleration, a second sensor for determining rotational acceleration, a battery, a wireless battery charging component, and a communication transmitter for transmitting an indication signal in response to an impact experienced by the user, the battery being mounted in the first or second end portions of the printed circuit board, the wireless battery charging component being mounted in the first or second end portions of the printed circuit board, the communication transmitter being mounted in the middle portion of the printed circuit board;
 overlaying a second layer of material over the flexible printed circuit board and the first layer;
 heating at least one of the first and second layers to help conform the plurality of components on the flexible circuit board to the first and second layers of material to create the custom mouth guard, the custom mouth guard having a front portion with a generally arched-shaped peripheral side surface for facing the buccal region of a mouth of a user, the printed circuit board being within the front portion of the custom mouth guard, the wireless battery charging component and the communication transmitter facing outwardly toward the buccal region; and
 storing impact threshold data on the memory device of the flexible printed circuit board, the impact threshold data being based on biometric information associated with the user.

21. A method for manufacturing a custom mouth guard that detects impact forces of a user, comprising:
 conforming a first layer of material to a model of the user's maxillary region, the model includes the user's replicated teeth, the model being created from an intra-oral scan of the user's maxillary region;
 placing a flexible printed circuit board onto the first layer, the flexible printed circuit having a first end portion located adjacent to one molar region on the replicated teeth, a second end portion located adjacent to the other molar region on the replicated teeth, a middle portion adjacent to an incisor region on the replicated teeth, and at least one bridge portion adjacent to one of the first and second end portions, the first and second end portions having widths that are greater than the at least one bridge portion, the flexible printed circuit having a plurality of components including at least a processor, a memory device, a first sensor for determining linear acceleration, a second sensor for determining rotational acceleration, a battery, a wireless battery charging component, and a communication transmitter for transmitting an indication signal in response to an impact experienced by the user, the battery being mounted in the first or second end portions of the printed circuit board, the wireless battery charging component being mounted in the first or second end portions of the printed circuit board, the communication transmitter being mounted in the middle portion of the printed circuit board, at least one of the first and second sensors being mounted in the middle portion of the printed circuit board;
 overlaying a second layer of material over the flexible printed circuit board and the first layer;
 heating at least one of the first and second layers to help conform the plurality of components on the flexible circuit board to the first and second layers of material to create the custom mouth guard, the custom mouth guard having a front portion with a generally arched-shaped peripheral side surface for facing the buccal region of a mouth of a user, the printed circuit board being within the front portion of the custom mouth guard, the wireless battery charging component and the communication transmitter facing outwardly toward the buccal region.

\* \* \* \* \*